United States Patent [19]

Crowley

[11] 4,441,609

[45] Apr. 10, 1984

[54] PHARMACEUTICAL COMPOSITIONS

[75] Inventor: Patrick J. Crowley, Worthing, England

[73] Assignee: Beecham Group Limited, England

[21] Appl. No.: 17,365

[22] Filed: Mar. 5, 1979

Related U.S. Application Data

[62] Division of Ser. No. 949,028, Oct. 6, 1978, abandoned.

[30] Foreign Application Priority Data

Oct. 11, 1977 [GB] United Kingdom ............... 42191/77

[51] Int. Cl.$^3$ ................................................. A45F 3/00
[52] U.S. Cl. .................................. 206/204; 206/524.4; 424/271
[58] Field of Search ................... 206/524.4, 524.5, 204

[56] References Cited

U.S. PATENT DOCUMENTS 3,128,135 4/1964 Ege ..................................... 206/204
3,567,085 3/1971 Flores .................................. 206/204

OTHER PUBLICATIONS

Dewent FOUMDOC #72840w/44 Abstract DT2517-316 published 10/23/75.

Primary Examiner—Robert I. Smith
Attorney, Agent, or Firm—Jacobs & Jacobs

[57] ABSTRACT

A dry unit-dose pharmaceutical composition suitable for oral administration which composition comprises 20 mg to 1500 mg of amoxycillin trihydrate, 20 mg to 500 mg of potassium clavulanate and a pharmaceutically acceptable carrier with the proviso that the weight ratio of amoxycillin trihydrate to potassium clavulanate is from 6:1 to 1:1; has favored storage properties. Such compositions are presented in enclosed containers which they also contain a desiccant.

8 Claims, No Drawings

PHARMACEUTICAL COMPOSITIONS

This is a division of Ser. No. 949,028 filed Oct. 6, 1978 and now abandoned.

The present invention relates to pharmaceutical compositions for oral administration in the treatment of bacterial infections.

Amoxycillin and its salts were disclosed in British Patent Specification No. 1241844 as antibacterial agents useful in the treatment of gram-negative and gram-positive bacterial infections. However, certain bacteria are resistant to amoxycillin by virtue of the β-lactamase they produce. Clavulanate salts were disclosed in British Patent Specification No. 1508977 as β-lactamase inhibitors capable of enhancing the antibacterial effects of penicillins and cephalosporins.

We have now found that when amoxycillin trihydrate is formulated in a composition together with potassium clavulanate, the resulting composition has a greater storage life than analogous compositions in which the potassium clavulanate is replaced by sodium clavulanate or the like or if the amoxycillin trihydrate is replaced by the sodium amoxycillin. This enhancement of storage stability is particularly effective when the materials present in the composition are dry, that is essentially water-free, for example as obtained by pre-drying to remove moisture other than the water of crystallisation present in the amoxycillin trihydrate.

Accordingly the present invention provides a dry unit-dose pharmaceutical composition suitable for oral administration which composition comprises 20 mg to 1500 mg of amoxycillin trihydrate, 20 mg to 500 mg of potassium clavulanate and a pharmaceutically acceptable carrier with the proviso that the weight ratio of amoxycillin trihydrate to potassium clavulanate is from 6:1 to 1:1. When weights or weight ratios are referred to herein said weights or weight ratios are based on the weight of parent antibiotic (amoxycillin or clavulanic acid) theoretically available from the composition.

More suitably the weight ratio of amoxycillin trihydrate to potassium clavulanate is from 5:1 to 2:1 for example 5:1, 4:1, 3:1 or 2:1.

Preferred weight ratios of amoxycillin trihydrate to potassium clavulanate vary from about 3:1 to about 2:1 a ratio of about 2:1 being particularly preferred.

In general the oral dosage unit of this invention will contain from 125 mg to 1250 mg of amoxycillin trihydrate for example it may contain about 225, 250, 290, 435, 500, 580, 870 or 1000 mg of amoxycillin trihydrate.

In general the oral dosage unit of this invention will contain from 40 to 300 mg of potassium clavulanate for example it may contain about 50, 60, 75, 100, 120, 125, 150, 200, 240, 250 or 300 mg of potassium clavulanate.

From the foregoing it will be realised that certain preferred compositions of this invention comprise from 80 mg to 600 mg of amoxycillin trihydrate and from 40 mg to 300 mg of potassium clavulanate with the proviso that the weight ratio of amoxycillin trihydrate to potassium clavulanate is 2:1.

Suitable amounts of potassium clavulanate for use in those compositions include the aforementioned approximately 50, 60, 75, 100, 120, 125, 150, 200, 240, 250 or 300 mgs.

The oral dosage unit of this invention may be in the form of a tablet, capsule, syrup, powder or granulate for reconstitution present in a sachet or the like. Shaped forms of the composition such as tablets or capsules are particularly suitable.

Certain preferred compositions, especially shaped compositions of this invention will contain about 125-150 mg of amoxycillin trihydrate and about 62.5-75 mg of potassium clavulanate. Other preferred compositions, especially shaped compositions of this invention will contain about 250-300 mg of amoxycillin trihydrate and about 125-150 mg of potassium clavulanate.

Such compositions may contain one or more conventional fillers such as microcrystalline cellulose, lubricants such as magnesium stearate, disintegrants such as sodium starch glycollate or other similar known agents. In addition such compositions may contain flavouring agents, preservatives, colouring agents and the like. The materials present in such compositions should be water-free and preferably pre-dried.

Other typical agents which may be used in the carrier include microfine cellulose (as a filler), calcium carbonate or magnesium carbonate (usually light magnesium carbonate) (as fillers), starch (as a disintegrant) and glycine (as a disintegrant).

Tablets according to this invention may be film coated if desired, for example with a coat that delays ingress of moisture. Suitable agents for such film coats include methacrylic acid methacrylate co-polymers, and natural resins such as shellac or copal resins or their conventional modifications.

The compositions of this invention show an especially improved storage life if they are packed in such a manner as that ingress of moisture is prevented. This may be conveniently effected by packing in a screw-capped bottle or some other similar effectively closed container such as a screw top metal cannister.

Thus the present invention further provides a packaged pharmaceutical composition of enhanced storage stability which comprises a container closed to prevent ingress of moisture and which contains one or more unit-dose compositions as hereinbefore described.

It is particularly advantageous to include a desiccant within the package.

Thus in a further aspect this invention provides a packaged pharmaceutical composition of enhanced storage stability which comprises a container closed to prevent ingress of moisture and which contains one or more unit-dose compositions as hereinbefore described and a desiccant.

Suitable desiccants will be non-toxic and include Silica Gel or crystalline sodium, potassium or calcium aluminosilicate (commonly termed "Molecular Sieves"). Such desiccants may be included in sachets or capsules within the packaging or may be enclosed in a receptacle or separate compartment, for example in the cap or on the floor of the container.

In yet another aspect of this invention provides a method of prolonging the storage life of a composition as hereinbefore described in a container which comprises storing said composition in an atmosphere maintained dry by the presence of a desiccant in the container.

Suitable containers and desiccants are as hereinbefore described.

The dosage form of this invention may be fabricated in the conventional manner, for example by blending and compressing to form tablets, blending and filling into capsules or blending and filling into sachets and the like.

Thus this invention provides a process for the preparation of preparing a composition as hereinbefore described which comprises bringing into association the components of said compositions.

Suitably the unit-dose compositions when prepared are filled into a container which is then closed to prevent ingress of moisture.

It is preferable that the formulation of the composition is carried out in a dry atmosphere, e.g. one containing less than 30% relative humidity and more suitably one containing less than 20% relative humidity.

In the following examples, which illustrate the invention, the compositions were formulated under a dry atmosphere.

EXAMPLE 1

Tablets of the following compositions were prepared:

| Ingredients | mg per tablet | | | |
|---|---|---|---|---|
| Amoxycillin Trihydrate | 290 | 290 | 580 | 580 |
| Potassium Clavulanate | 60 | 150 | 120 | 300 |
| Colloidal Silica | 3.0 | 3.8 | 6.0 | 7.6 |
| Sodium Starch Glycollate (dried) | 7.2 | 8.9 | 14.4 | 17.8 |
| Magnesium Stearate | 5.0 | 6.2 | 10.0 | 12.4 |
| Microcrystalline Cellulose to (Dried) | 436.0 | 550.0 | 872.0 | 1100.0 |

The tablets were prepared by passing the ingredients through a 30 mesh (British Standard) sieve and then blending them. The mix was then compressed in a conventional tablet machine. The tablets were prepared in a batch of about 5000 tablets.

The preparation of the tablets was carried out in a dry atmosphere (relative humidity less than 30%).

EXAMPLE 2

Tablets having the same composition as those of Example 1 were also prepared by the following process: the amoxycillin trihydrate and potassium clavulanate were seived, blended with a proportion of the disintegrant and lubricant (about ½ of each) and compressed to a uniform density on a tablet machine. The pressed slugs were milled to produce granules of a uniform size and density and the remainder of the ingredients then mixed in. The blend was then compressed to tablets on a conventional tablet machine. The tablets were prepared in a batch of about 5000 tablets.

The preparation of the tablets was carried out in a dry atmosphere (relative humidity less than 30%).

EXAMPLE 3

Fifteen of the 290/150 mg tablets of Example 1 were packed in an amber glass bottle and the bottle closed with its metal screw cap to exclude ingress of moisture. Prior to capping a sachet of molecular sieve (sodium aluminosilicate (type 4A) (1.0 g) in a moisture-permeable sachet) was included.

A bottle of 290/60 mg tablets were similarly prepared.

After the storage the potencies of the ingredients were found to be as follows:

| Strength | Storage Period (months) | Storage Temperature (°C.) | Stability (% of initial potency) | |
|---|---|---|---|---|
| | | | Trihydrate Amoxycillin | Potassium Clavulanate |
| 290/60 | Initial | | 100 | 100 |
| | 2 | 20 | 97 | 100 |
| | | 30 | 99 | 100 |
| | | 37 | 100 | 98 |
| | 4 | 30 | 96 | 101 |
| | | 37 | 96 | 100 |
| 290/150 | Initial | | 100 | 100 |
| | 2 | 30 | 99 | 105 |
| | | 37 | 99 | 104 |

Similar capped bottles may be prepared in which the molecular sieve is replaced by silica gel.

After further storage the observed potencies for these forms were:

| Strength | Storage Period (months) | Storage Temp. (°C.). | Stability (% initial) | |
|---|---|---|---|---|
| | | | Amoxycillin Trihydrate | Potassium Clavulanate |
| 290/60 | 8 | 20 | 99 | 95 |
| | | 30 | 98 | 90 |
| | 12 | 20 | 98 | 95 |
| 290/150 | 4 | 30 | 96 | 102 |
| | | 37 | 97 | 100 |
| | 8 | 20 | 105 | 99 |
| | | 30 | 101 | 99 |
| | | 37 | 98 | 95 |
| | 12 | 20 | 103 | 101 |
| | | 30 | 97 | 104 |
| | | 37 | 95 | 99 |

EXAMPLE 4

A single-dose sachet containing a dry powder to be reconstituted with water before administration may be prepared containing the following:

| | mg per dose |
|---|---|
| Amoxycillin Trihydrate | 145 |
| Potassium Clavulanate | 75 |
| Buffering Agent | 10.0 |
| Flavour | 55.0 |
| Desiccating Agent | 500.0 |
| Glidant | 20.0 |
| Sugar to | 3300.0 |

EXAMPLE 5

Tablets of the following compositions were prepared:

| Ingredient | mg per tablet |
|---|---|
| Amoxycillin Trihydrate | equivalent to 125 mg of pure non-hydrated amoxycillin |
| Potassium Clavulanate | equivalent to 62.5 mg of pure clavulanic acid |
| Cross-linked polyvinylpyrollidone (disintegrant) | 50.0 |
| Monoammonium Glycrrhizinate (flavour enhancer) | 15.0 |
| Flavours | 32.5 |
| Magnesium stearate (lubricant) | 20.0 |
| Microcrystalline cellulose to | 750.0 |

The tablets were prepared in batches of 2000 by passing the ingredients through a 30 mesh sieve, blending together and compressing on a suitable tablet machine.

Fifteen of the above tablets were packed in amber glass bottles and the bottle closed with a metal screw-cap to exclude ingress of moisture. Prior to capping a sachet of molecular sieve (1.0 g) was included.

After storage the potencies of the ingredients were found to be as follows:

| Storage Period (months) | Storage Temp. (°C.) | Stability (% of initial potency) | |
|---|---|---|---|
| | | Amoxycillin trihydrate | Potassium Clavulanate |
| Initial | | 100 | 100 |
| 2 | 37 | 102 | 100 |
| 4 | 30 | 98 | 100 |
| | 37 | 94 | 101 |
| 8 | 20 | 102 | 96 |
| | 30 | 99 | 96 |
| | 37 | 92 | 91 |

EXAMPLE 6

Tablets of the following composition were prepared:

| Ingredient | mg/tablet |
|---|---|
| Amoxycillin Trihydrate | equivalent to 250 mg of pure non-hydrated amoxycillin |
| Potassium clavulanate | equivalent to 125 mg of pure clavulanic acid |
| Microcrystalline cellulose | 100 |
| Sodium Starch Glycollate | 15 |
| Magnesium Stearate | 8 |
| Microcrystalline Cellulose to | 765 |

The tablets were prepared as follows: The active ingredients were passed through a 16 mesh screen and blended with the microfine cellulose, a portion of the microcrystalline cellulose and a portion of the magnesium stearate. The mix was compressed to a uniform density on a suitable tablet machine. The pressed slugs were milled to produce granules of uniform size and density and the remainder of the ingredients were then incorporated. The mix was blended and compressed to tablets on a suitable machine.

| Storage Period (Months) | Storage Temp. (°C.) | Stability (% initial) | |
|---|---|---|---|
| | | Amoxycillin Trihydrate | Potassium Clavulanate |
| Initial | | 100 | 100 |
| 2 | 37 | 97 | 101 |
| 4 | 30 | 100 | 99 |
| | 37 | 98 | 99 |
| 8 | 20 | 101 | 98 |
| | 30 | 97 | 99 |
| | 37 | 96 | 100 |

EXAMPLE 7

Tablets of the following composition were prepared:

| Ingredient | mg/tablet |
|---|---|
| Amoxycillin Trihydrate | equivalent to 250 mg of pure non-hydrated amoxycillin |
| Potassium clavulanate | equivalent to 125 mg of pure clavulanic acid |
| Microcrystalline cellulose | 250 |
| Cross-linked polyvinylpyrollidone | 45 |
| Magnesium Stearate | 11.8 |
| Glycine to | 975 |

The preceeding tablets were prepared as follows:

The amoxycillin trihydrate and glycine were milled to fine powders on a suitable machine, the potassium clavulanate was passed through a 30 mesh screen, all three materials were then blended with a portion of the magnesium stearate and compressed to a uniform density on a suitable tablet machine. The pressed slugs were milled to produce granules of a uniform size and density and the remainder of the ingredients were then added. The mix was blended and compressed to tablets on a suitable machine.

Fifteen of the above tablets were put into an ambler glass bottle and the bottle closed by a screw cap. The storage properties of the composition is illustrated by the following:

| Storage Period (months) | Storage Temp. (°C.). | Stability (% initial) | |
|---|---|---|---|
| | | Amoxycillin Trihydrate | Potassium Clavulanate |
| Initial | | 100 | 100 |
| 2 | 37 | 100 | 98 |
| 4 | 30 | 99 | 97 |
| | 37 | 95 | 95 |

EXAMPLE 8

Tablets of the following composition were prepared:

| Ingredient | mg/tablet |
|---|---|
| Amoxycillin trihydrate | equivalent to 250 mg of pure non-hydrated amoxycillin |
| Potassium clavulanate | equivalent to 125 mg of pure clavulanic acid |
| Calcium Carbonate | 175 |
| Heavy Magnesium Carbonate | 110 |
| Cross-linked polyvinylpyrollidone | 75 |
| Magnesium Stearate | 19.5 |
| Microcrystalline Cellulose to | 1000 |

The preceeding tablets were prepared as follows:

The amoxycillin trihydrate, potassium clavulanate and calcium carbonate were passed through a 30 mesh screen and then blended with microcrystalline cellulose and a proportion of the magnesium stearate. The mix was compressed to a uniform density on a suitable tablet machine and the pressed slugs then milled to produce granules of suitable size and density. The heavy magnesium carbonate was passed through a 30 mesh screen and then blended with the milled slugs, cross-linked PVP and the remainder of the magnesium stearate. The mix was compressed to tablets on a suitable machine.

Twenty five tablets as above were filled into a metal cannister, a sachet of molecular sieve added (1 g) and the cannister and contents stored. The results of this test were as follows:

| Storage Period (Months) | Storage Temp. (°C.) | Stability (% initial) | |
|---|---|---|---|
| | | Amoxycillin Trihydrate | Potassium Clavulanate |
| Initial | | 100 | 100 |
| 2 | 37 | 98 | 97 |
| 4 | 30 | 100 | 96 |
| | 37 | 97 | 94 |

EXAMPLE 9

The tablets of Examples 7 and 8 were also produced in film coated form as follows:

The priming coat ingredients were added to an organic solvent (a dichloromethane/methanol mixture) and a high speed homogenises used to disperse/dissolve the materials. The fine suspension thus obtained was sprayed from an atomizer nozzle onto a rotating bed of 2000-3000 tablets through which warm air is passed to remove the solvent. The rate of spraying was such that an even application of coat was achieved and the tablets did not adhere to each other. The top coat was then applied in the same manner. Details of suitable coating materials are given below:

| Priming Coat Composition | |
|---|---|
| Ingredients | mg/tablet (approx.) |
| Hydroxylpropylmethyl cellulose film-formers | 9.0 |
| Ethyl cellulose | 2.25 |
| Diethyl Phthalate (plasticizer) | 2.70 |
| Titanium Dioxide (pigment) | 4.0 |
| | 17.95 |
| Top - Coat (Type A) | |
| Methacrylic acid - methylacrylate co-polymer | 11.7 |
| Diethyl Phthalate | 2.3 |
| Top - Coat (Type B) | |
| Opagloss (modified Shellac) | 7.0 |

EXAMPLE 10

Two part gelatin capsules may be filled with the ingredients specified in Example 6. The blend obtained immediately prior to final compression in to tablet form in Example 6 may be filled into capsules by hand or on a filling machine.

I claim:

1. A packaged pharmaceutical composition of enhanced storage stability which comprises a closed container containing one or more unit-dose compositions suitable for oral administration each dosage unit of which comprises 20 mg to 1500 mg of amoxycillin trihydrate, 20 mg to 500 mg of potassium clavulanate and a pharmaceutically acceptable carrier with the proviso that the weight ratio of amoxycillin trihydrate to potassium clavulanate is from 6:1 to 1:1 and a desiccant.

2. A packaged pharmaceutical composition according to claim 1 wherein the container is operable and closable by means of a screw-top.

3. A packaged pharmaceutical composition according to claim 1 wherein the desiccant is silica gel.

4. A packaged pharmaceutical composition according to claim 1 wherein the desiccant is crystalline sodium, potassium or calcium aluminosilicate.

5. A method of prolonging the storage life of dry amoxycillin trihydrate which comprises adding to said amoxycillin trihydrate a storage life prolonging amount of potassium clavulanate so that the weight ratio of amoxycillin trihydrate to potassium clavulanate is from 6:1 to 1:1.

6. A method according to claim 5 wherein the ratio is 5:1 to 2:1.

7. A method according to claim 5 wherein the ratio is 3:1 to 2:1.

8. A method according to claim 5 wherein said amoxycillin trihydrate and potassium clavulanate are packed in such a manner that ingress of moisture is prevented.

* * * * *